(12) United States Patent
Nair et al.

(10) Patent No.: US 7,737,121 B2
(45) Date of Patent: Jun. 15, 2010

(54) INSULIN SECRETION BY ANTHOCYANINS AND ANTHOCYANIDINS

(75) Inventors: Muraleedharan G. Nair, Okemos, MI (US); Bolleddula Jayaprakasam, East Lansing, MI (US); L. Karl Olson, East Lansing, MI (US); Shaiju K. Vareed, East Lansing, MI (US)

(73) Assignee: Board of Trustees of Michigan State University, Lansing, MI (US)

( * ) Notice: Subject to any disclaimer, the term of this patent is extended or adjusted under 35 U.S.C. 154(b) by 336 days.

(21) Appl. No.: 11/071,929

(22) Filed: Mar. 4, 2005

(65) Prior Publication Data

US 2006/0025353 A1    Feb. 2, 2006

Related U.S. Application Data

(60) Provisional application No. 60/591,806, filed on Jul. 29, 2004.

(51) Int. Cl.
*A61K 31/7048* (2006.01)
*A61K 31/70* (2006.01)

(52) U.S. Cl. ........................................ 514/27; 514/456

(58) Field of Classification Search .................. 514/27, 514/456
See application file for complete search history.

(56) References Cited

U.S. PATENT DOCUMENTS

| | | | |
|---|---|---|---|
| 6,194,469 B1 | 2/2001 | Nair et al. | |
| 6,423,365 B1 | 7/2002 | Nair | |
| 6,623,743 B1 | 9/2003 | Nair et al. | |
| 6,656,914 B2 | 12/2003 | Nair et al. | |
| 6,676,978 B1 | 1/2004 | Nair | |

2004/0131749 A1 *  7/2004  Grabiel et al. .............. 426/629

OTHER PUBLICATIONS

Nair et al Agricultural and Food Chemistry, 2002, 50, 2519-2523.*
Osawa et al J. Nutrition, 2003, 133, 2125-2130.*
Vanella et al, Cell Biol. Toxicol. 2003, 19, 243-252.*
Ross, S.A., et al., Chemistry and Biochemistry of diabetes. Chem. Rev. 104 1255-1282 (2004).
Jovanovic, L., et al. Type-2 diabetes: The epidemic of new millennium. Ann. Clin. Lab. Sci. 29 33-42 (1999).
Henquin,J.C., Diabetes 49 1751-1760(2000).
Pfeiffer, A.F.H., Oral hypoglycemic agents; Sulfonylureas and meglitinides. In B.J. Goldstein, et al., (Eds.), Test book of Type-2 Diabetes. Martin Dunitz Ltd., London pp. 77-85 (2003).
Blakely, S., et al., J. Nutr. 133 2838-2844 (2003).
Jayaprakasam, B., et al., Potent lipid peroxidation inhibitors from Withania somnifera. Tetrahedron 60 3109-3121 (2004).
Duthie, G.G., et al., Nutr. Res. Rev. 13 79-106 (2000).
Kang, S.Y., et al., Canc. Lett. 194 13-19 (2003).
Van Velden, D.P., et al., Ann. New York Acad. Sci. 957 337-340 (2002).
Wang, H., et al., J. Nat. Prod. 62 294-296 (1999).
Tsuda, T., et al., J. Nut. 133 2125-2130(2003).
Espin, J.C., et al., J. Agri. Food Chem. 48 1588-1592 (2000).
Kim, D. K., et al., Arch. Pharm. Res. 21 787-789(1998).
Yamahara, J., et al., Yakugaku Zasshi 101 86-90 (1981).
Seeram, N. P., et al., J. Agri. Food chem.. 50 2519-2523 (2002).
Francis, J.A., et al., Helv. Chim. Acta 87 317-326 (2004).
Christison, G.B., et al., Med. Boil. Eng. Comp 31 284-290 (1993).
Anderson, R.A., et al., J. Agric. Food Chem. 50 7182-7186 (2002).
Anderson, R.A., et al., J. Agric. Food Chem. 52 65-70 (2004).
Landrault, N., et al., J. Agric. Food Chem. 51 311-3188 (2003).

* cited by examiner

*Primary Examiner*—Shaojia Anna Jiang
*Assistant Examiner*—Ganapathy Krishnan
(74) *Attorney, Agent, or Firm*—Avery N. Goldstein

(57) ABSTRACT

A method for stimulating insulin secretion by anthocyanidins and anthocyanins is described. The secretion can be in vivo in mammals, including humans, or in vitro.

13 Claims, 4 Drawing Sheets

|   | R   | R'    | R"    |
|---|-----|-------|-------|
| 1 | Glc | OH    | H     |
| 2 | Glc | OH    | OH    |
| 3 | Gal | OH    | H     |
| 4 | Gal | H     | H     |
| 5 | H   | OH    | H     |
| 6 | H   | OH    | OH    |
| 7 | H   | H     | H     |
| 8 | H   | OCH$_3$ | OCH$_3$ |
| 9 | H   | OCH$_3$ | OH    |

INSULIN SECRETION BY ANTHOCYANINS AND ANTHOCYANIDINS

CROSS-REFERENCE TO RELATED APPLICATION

This application relies for priority on Provisional Patent Application Ser. No. 60/591,806, filed Jul. 29, 2004.

GOVERNMENT RIGHTS

This invention was funded under USDA Grant No. 2003-35504-13618. The U.S. Government has certain rights to this invention.

BACKGROUND OF THE INVENTION (1) Field of the Invention

The present invention relates to a method which uses anthocyanins, anthocyanidins or mixtures thereof to increase insulin production by cells. The present invention also relates to compositions to be used in the method for producing the increase in production of the insulin. The method and compositions can be in vivo or in vitro.

(2) Description of Related Art

The function of insulin is to maintain normal blood glucose levels either by suppression of glucose output from liver or by the stimulation of glucose uptake and its metabolism (Ross, S. A., et al., Chemistry and Biochemistry of diabetes. Chem. Rev. 104 1255-1282 (2004)). Insufficient release of insulin or loss of insulin action at target tissues causes aberrant glucose and lipid metabolism. This results in elevated glucose levels in the blood, a hallmark of diabetes (Jovanovic, L., et al. Type-2 diabetes: The epidemic of new millennium. Ann. Clin. Lab. Sci. 29 33-42 (1999)). There are two types of diabetes, type-1 (insulin-dependent diabetes) and type-2 diabetes (non-insulin-dependent diabetes). Type-1 diabetes results from autoimmune destruction of pancreatic β-cells, the cells that secrete insulin, which leads into insulin insufficiency. Type-2 diabetes is more prevalent and is caused by the inability of β-cells to secrete sufficient amounts of insulin to overcome insulin resistance established by genetic and environmental factors (Henquin, J. C., Diabetes 49 1751-1760 (2000)). The insulin resistance is a disorder in which insulin inadequately stimulates glucose transport in skeletal muscle and fat and inadequately suppresses hepatic glucose production. The mechanisms involved that prevent the β-cell from secreting sufficient amounts of insulin to overcome peripheral insulin resistance remain to be established. Oral hypoglycemic agents that directly stimulate insulin release from β-cells (e.g. sulfonylurea based drugs), however, have shown that insulin secretion from islets of type-2 diabetic patients can be elevated sufficiently to overcome peripheral insulin resistance and normalize blood glucose levels. One of the disadvantages of using sulfonylurea-based drugs is that it fails to control normal blood glucose levels (Pfeiffer, A. F. H., Oral hypoglycemic agents: Sulfonylureas and meglitinides. In B. J. Goldstein, et al., (Eds.), Test book of Type-2 Diabetes. Martin Dunitz Ltd., London pp. 77-85 (2003)). These drugs also adversely affect the ability of S-cells to secrete insulin and cause weight gain ((Pfeiffer, A. F. H., Oral hypoglycemic agents: Sulfonylureas and meglitinides. In B. J. Goldstein, et al., (Eds.), Test book of Type-2 Diabetes. Martin Dunitz Ltd., London pp. 77-85 (2003)). Hence, there is a role for dietary constituents that can regulate blood glucose level or induce insulin production by pancreatic β-cell.

The consumption of a diet low in fat and rich in antioxidants reduces the risk of obesity and insulin resistance (Blakely, S., et al., J. Nutr. 133 2838-2844 (2003)). Anthocyanins belong to antioxidant polyphenols and are present in various foods and beverages. Consumption of anthocyanins is associated with reduced risk of several degenerative diseases such as atheroscelerosis, cardiovascular disease, cancer and diabetes (Jayaprakasam, B., et al., Potent lipid peroxidation inhibitors from Withania somnifera. Tetrahedron 60 3109-3121 (2004)). These compounds are well-known free radical scavengers and reported as potential chemopreventive agents (Duthie, G. G., et al., Nutr. Res. Rev. 13 79-106 (2000)). For example, serum antioxidant capacity was increased by the consumption of strawberries, cherries, and red wine (Kang, S. Y., et al., Canc. Lett. 194 13-19 (2003); Van Velden, D. P., et al., Ann. New York Acad. Sci. 957 337-340 (2002); and Wang, H., et al., J. Nat. Prod. 62 294-296 (1999)). Recent studies demonstrated that the anthocyanin, cyanidin 3-glucoside, reduced the high fat diet induced obesity in mice (Tsuda, T., et al., J. Nut. 133 2125-2130 (2003)). Therefore, the natural colorants present in the food have attracted consumers due to their safety, nutritional and therapeutic values (Espin, J. C., et al., J. Agri. Food Chem. 48 1588-1592 (2000)). Since anthocyanins are widely consumed, additional biological activities of these compounds will be of great interest.

The fruits of the Cornus species are a rich source of anthocyanins. The fruits of Cornus mas L., also known as the European and Asiatic Cornelian cherry, are used in the preparation of beverages in Europe (Millspaugh, C. F., In American Medicinal Plants; Dover Publications: New York, 282 (1974)). In traditional medicine, Cornus officinalis fruits are known for their analgesic and diuretic activities (Kim, D. K., et al., Arch. Pharm. Res. 21 787-789 (1998)). The Cornus fruits are also one of the major constituents of several antidiabetic herbal preparations in Asian countries (Yamahara, J., et al., Yakugaku Zasshi 101 86-90 (1981)). Our earlier investigation of the fruits of C. mas and C. officinalis revealed that both contained high levels of anthocyanins (Seeram, N. P., et al., J. Agri. Food chem. 50 2519-2523 (2002)).

OBJECTS

Therefore it is an object of the present invention to provide a method and compositions for increasing insulin production in vitro or in vivo. Further objects will become apparent from the following description and the drawings.

SUMMARY OF THE INVENTION

The present invention relates to a method for increasing insulin secretion by pancreatic cells which secrete the insulin which comprises:

providing an anthocyanin or anthocyanidin or mixture thereof with the pancreatic beta cells to increase insulin secretion over the insulin secretion without the anthocyanin. The anthocyanin is preferably isolated from fruits, vegetables and flowers. Preferably in the method the anthocyanin is selected from the group consisting of cyanidin-3-glycoside, delphinidin-3-glycoside, pelargonidin-3-glycoside and mixtures thereof. The pancreatic cells can be in vivo. The pancreatic cells can be in vitro. Preferably in the method the anthocyanidin or anthocyanin or mixture thereof is isolated and purified.

The present invention also relates to anthocyanin or anthocyanidin or mixture thereof as a dosage unit for use in increasing insulin production from pancreatic cells in vivo.

Preferably in the composition, the anthocyanin is isolated from fruits, vegetables and flowers. Preferably in the composition the anthocyanin is selected from the group consisting of cyanidin-3-glycoside, delphinidin-3-glycoside, pelargonidin-3-glycoside and mixtures thereof. Preferably in the composition the anthocyanidin or anthocyanin or mixture thereof is isolated and purified. A "glycoside" is any compound that contains a carbohydrate molecule (sugar), particularly any such natural product in plants, convertible, by hydrolytic cleavage, into sugar and a nonsugar component (aglycone), and named specifically for the sugar contained, as glucoside (glucose), pentoside (pentose), fructoside (fructose), etc.

Anthocyanins are responsible for a variety of bright colors including red, blue, and purple in fruits, vegetables, and flowers and consumed as dietary polyphenols. Anthocyanin containing fruits are implicated in decreased coronary heart diseases and used in antidiabetic preparations. The present invention shows the ability of anthocyanins, cyanidin-3-glucoside (1), delphinidin-3-glucoside (2), cyanidin-3-galactoside (3) and pelargonidin-3-galactoside (4); and anthocyanidins, cyanidin (5), delphinidn (6), pelargonidin (7), malvidin (8), and petunidin (9) to stimulate insulin secretion by rodent pancreatic beta cells (INS-1 813/32) in vitro. The compounds were tested in the presence of 4 and 10 mM glucose concentrations. Cyanidin-3-glucoside (1) and delphinidin-3-glucoside (2) were the most effective insulin secretagogues among the anthocyanins and anthocyanidins tested at 4 and 10 mM glucose concentrations. Pelargonidin-3-galactoside is one of the major anthocyanins and its aglycone, pelargonidin, caused a 1.4-fold increase in insulin secretion at 4 mM glucose concentration. Remaining of the anthocyanins and anthocyanidins tested had only marginal affects on insulin at 4 and 10 mM glucose concentrations.

DESCRIPTION OF PREFERRED EMBODIMENTS

EXAMPLES

Materials and Methods

Figure 1:
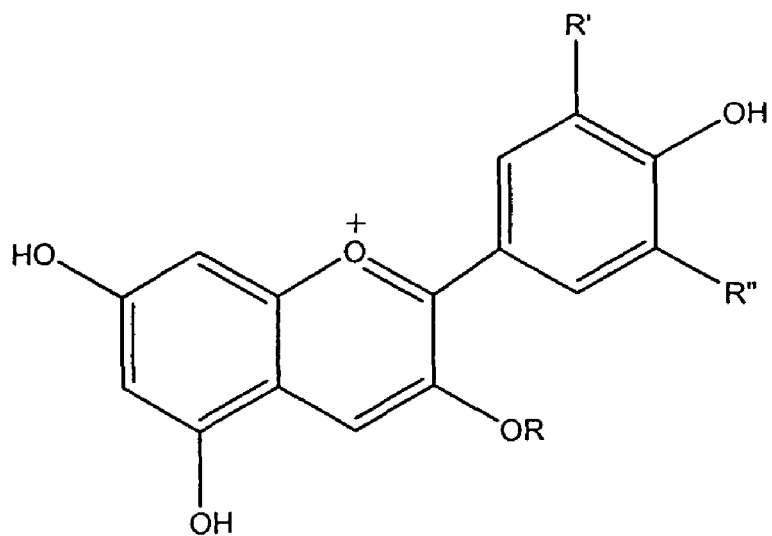
FIG. 1 is a drawing showing structures of anthocyanins 1-4 and anthocyanidins 5-9.

Chemicals. Fetal bovine serum (FBS) and RPMI-1640 medium were obtained from Invitrogen (Grand Island, N.Y.). All organic solvents used were ACS reagent grade. HEPES, penicillin-streptomycin, glutamine, sodium pyruvate, 2-mercaptoethanol, trypsin-EDTA, BSA (Bovine, Albumin; RIA Grade), Folin-Ciolatues reagent and chemicals used for the preparation of buffers were purchased from Sigma-Aldrich Chemical Co. (St. Louis, Mo.). The anthocyanidins, cyanidin, delphinidin, pelargonidin, malvidin, and petunidin, used in the assay were purchased from Chromadex (Laguna Hills, Calif.). Anthocyanins. Delphinidin-3-glucoside (2) was purified from *C. officinalis* fruits. Cyanidin-3-galactoside (3) and pelargonidin-3-galactoside (4) were isolated from *C. mas* fruits. Pure cyanidin-3-glucoside (1) used in this study was from our storage at −20° C.

Isolation and purification of anthocyanins. The *Cornus* fruits were blended with water (pH=3) and filtered. The filtrate was passed through XAD-16 amberlite resin in a column and the resin with the adsorbed anthocyanins was washed repeatedly with water (17). The XAD-16 resin was then eluted with acidic MeOH (pH=3) and the resulting solution was concentrated under reduced pressure to yield a crude anthocyanin fraction. This fraction was purified by MPLC column ($C_{18}$ silica) using MeOH:$H_2O$ (pH=3) under gradient conditions. The anthocyanins were eluted with MeOH:$H_2O$ (65:35,v/v) solvent system. The purity of the compounds was checked by HPLC (Waters Corp.) using Capcell $C_{18}$ analytical column under gradient conditions. The solvents used were A: TFA:$H_2O$ (99.9:0.1; v/v) and B: $H_2O$:$CH_3CN$: $CH_3COOH$:TFA (50.4: 48.5:1.0:0.1; v/v/v/v). The gradient was 20% B to 60% B in 26 min and to 20% B in 30 min at a flow rate of 0.8 ml/min. The peaks were detected at 520 nm using a PDA.

Insulin Secretion Studies. INS-1 832/13 cells (kindly provided by Dr Christopher Newgard, Duke University, NC) (18) were routinely cultured in 5% $CO_2$/air at 37° C. in RPMI-1640 medium containing 11.1 mM glucose and supplemented with 10% FBS (Fetal Bovine Serum), 10 mM HEPES, 100 U/ml penicillin, 100 μg/ml streptomycin, 4 mM Glutamine, 1 mM sodium pyruvate, and 50 μM 2-mercaptoethanol. Cells were passed weekly after trypsin-EDTA detachment. For static secretion studies, cells were plated on 24 well plates at a density of $0.64 \times 10^6$ cells per well and grown for 24 h. The cells were then cultured for an additional 24 h in RPMI-1640 containing 4 mM glucose and the supplements described above. Cells were then incubated twice for 30 min in Krebs Ringer Bicarbonate buffer (KRBB) containing 4 mM glucose and 0.1% BSA. Cells were rapidly washed with KRBB and incubated for 60 min KRBB containing 4 or 10 mM glucose with or without the indicated anthocyanins or anthocyanidins. The medium was then removed for determining insulin release. The cells were then washed twice with PBS and dissolved in 1 M NaOH. Cellular protein concentration was then determined by Lowry assay. Anthocyanins and anthocyanidins were dissolved in DMSO to obtain desired concentrations. Final concentration of DMSO was 0.1%. The insulin secreted into the medium by the cells was determined by radioimmuno assay and normalized to total cellular protein.

Radio Immuno Assay (RIA). The Kit for RIA was purchased from LINCO Research Inc. (St Charles, Mo.), and the assay was conducted according to the manufacturer's directions. Briefly, 0.1-10 ng of insulin standards (100 μl) were added to 12×75 mm test tubes. Similarly, samples (25 μl) from the insulin secretion studies were also added to the test tubes. To this, an aliquot (75 μl) of assay buffer was added. The $^{125}I$ labeled insulin (100 μl) was then added to each test tube. An aliquot of 100 μL anti rat insulin antibody was added to the tubes, mixed and incubated at 4° C. for 24 h and incubated further with 1 ml aliquot of the precipitating reagent for 20 min at 4° C. to precipitate the insulin bound to the antibody. The tubes were then centrifuged and the radioactivity was measured using a gamma counter.

Lowry protein Assay. The amount of protein in the assay wells was determined by Lowry method (Francis, J. A., et al., Helv. Chim. Acta 87 317-326 (2004)). The Lowry assay solution was prepared by combining the Lowry solution, $CuSO_4.5H_2O$ (1%), and sodium tartarate (1%). Briefly, the protein sample (100 µl) and Lowry mixture (1 mL) were mixed in a test tube (12×75). The Folin-Ciolatues reagent (100 µl) was added to these tubes, mixed, and incubated for 30 min at room temperature. The optical density of resulting solutions was read at 700 nm using a UV spectrophotometer.

Results and Discussion

The *Cornus* fruits are used in antidiabetic traditional Chinese prescription medicines such as "Hachimi-Gan" (Yamahara, J., et al., Yakugaku Zasshi, 101 86-90 (1981)). It was recently reported the quantification of anthocyanins in *Cornus* spp. fruits (Seeram, N. P., et al., *J. Agri. Food Chem.* 50 2519-2523 (2002)). The investigation of *Cornus* fruits indicated that the primary bioactive components in them were cyanidin, delphinidin and pelargonidin glycosides. Therefore, we have focused our attention on the insulin secreting ability of these anthocyanins and their aglycones using pancreatic beta cells in order to substantiate the anecdotal use of *Cornus* fruits in antidiabetic preparations. Petunidin, malvidin and peonidin aglycones were also included the assay since they are abundant in other fruits.

Anthocyanins are water-soluble compounds. The aqueous extracts of *C. mas* fruits contained sugars, bioflavonoids and anthocyanins and hence was fractionated by XAD-16 resin. The resulting anthocyanin fraction eluted from the resin was purified by MPLC to afford pure anthocyanins. The glucose-induced insulin production by INS-1 832/13 cells was determined at 4, 10 and 16 mM glucose concentrations and found that the insulin secretion reached a lag phase at 10 mM glucose concentration (data not presented). The glucose concentration at 4 mM level is representative of the normal glucose level in human (Christison, G. B., et al., *Med. Boil. Eng. Comp* 31 284-290 (1993)). The insulin secretion per mg of protein by cells at 10 mM glucose was three fold higher when compared to the insulin secretion at 4 mM glucose concentration.

Figure 2A:
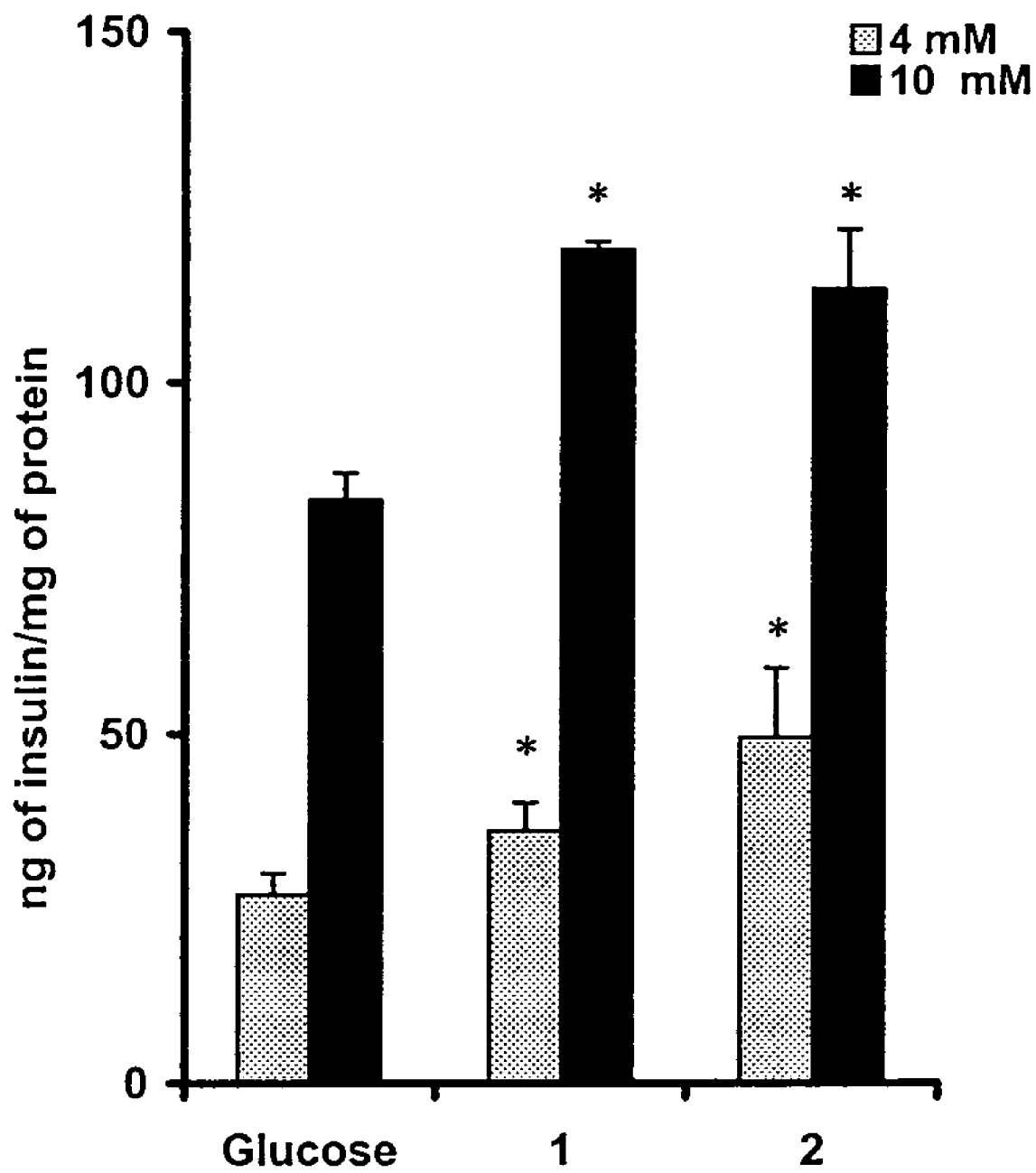
FIG. 2A is a graph showing the amount of insulin secreted per milligram of protein by compounds 1 and 2 and FIG. 2B by compounds 5 and 6 in the presence of 4 and 10 mM glucose. The final DMSO concentration in the assay wells was 0.1%. The results represented are the average of three or five independent experiments and each sample was assayed in duplicate. Insulin secretion by compounds 1, 2, 5 and 6 were significant at * (95% or p<0.05) or ** (99% or p<0.01) as determined by LSD using the t-test.
Figure 3:
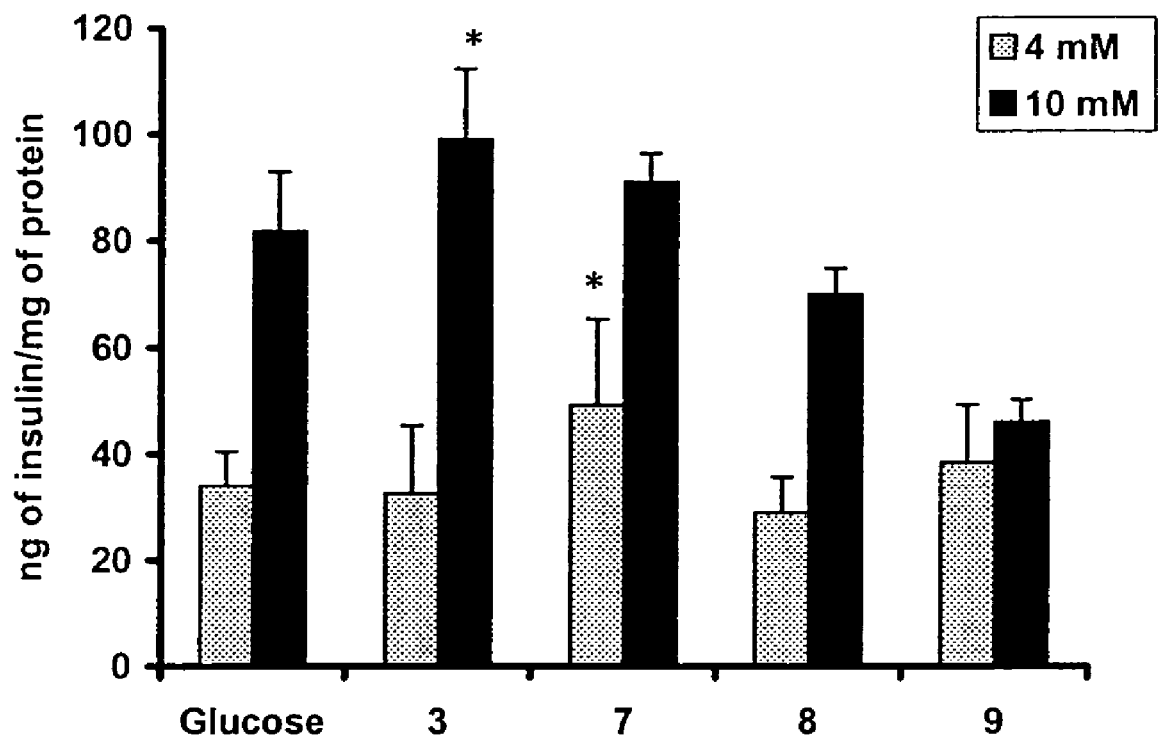
FIG. 3 is a graph showing the insulin secreted by compounds 3, 7-9 at 4 and 10 mM glucose concentrations. The amount of insulin secreted was normalized to milligram protein. The final DMSO concentration in the assay wells was 0.1%. The results represented are the average of three independent experiments and each sample was assayed in duplicate. Insulin secretion by compounds 3, 7-9 was significant at * (95% or $p \leqq 0.05$) as determined by LSD using the t-test.

Anthocyanins and anthocyanidins were also tested at 4 and 10 mM glucose loads in the cell growth medium. Anthocyanins and anthocyanidins were assayed initially at 50 µg/mL concentration. The anthocyanin, cyanidin 3-glucoside (1) showed an increase in insulin secretion at 4 mM glucose by 9 ng/mg of protein (1.3 fold) whereas it enhanced the insulin secretion by 1.43 fold (119 ng/mg protein) at 10 mM glucose concentration (FIG. 2A). Delphinidin-3-glucoside (2) was the most active anthocyanin tested and showed a 1.8-fold increase (49 ng/mg of protein) in insulin secretion at 4 mM glucose concentration. However, at 10 mM glucose it exhibited only a 1.4-fold (113 ng) increase (FIG. 2A) in insulin production. The insulin secreted by cells at 4 and 10 mM glucose concentrations in this assay were 27 and 83 ng of insulin per mg protein, respectively. The anthocyanins, cyanidin-3-galactoside (3) and pelargonidin-3-galactoside (4), did not increase the insulin secretion at 4 mM glucose concentration. However, cyanidin-3-galactoside showed an increase of 17 ng/mg of protein of insulin (1.2 fold) at 10 mM glucose concentration (FIG. 3). The pelargonidin-3-galactoside (4) was tested only once due to the limitation of sample.

The anthocyanin cyanidin-3-glucoside (1) was evaluated for dose dependent insulin secretion at 5, 10, 50, 100 and 250 µg/mL concentrations. The glucose concentration used in this assay was 4 mM level which is representative of the normal glucose level in human (Christison, G. B., et al., *Med. Boil. Eng. Comp.* 31 284-290 (1993)). At this concentration, untreated cells secreted 33 ng of insulin/mg of protein. The insulin secreted by cyanidin-3-glucoside (1) treated cells was 46 ng of insulin per mg protein at 5 µg/mL. However, there was no significant difference in insulin secretion at 10, 50, 100 and 250 µg/mL concentrations of compound 1. We did not have adequate supply of delphinidin-3-glucoside to conduct dose dependent assays.

Figure 2B:
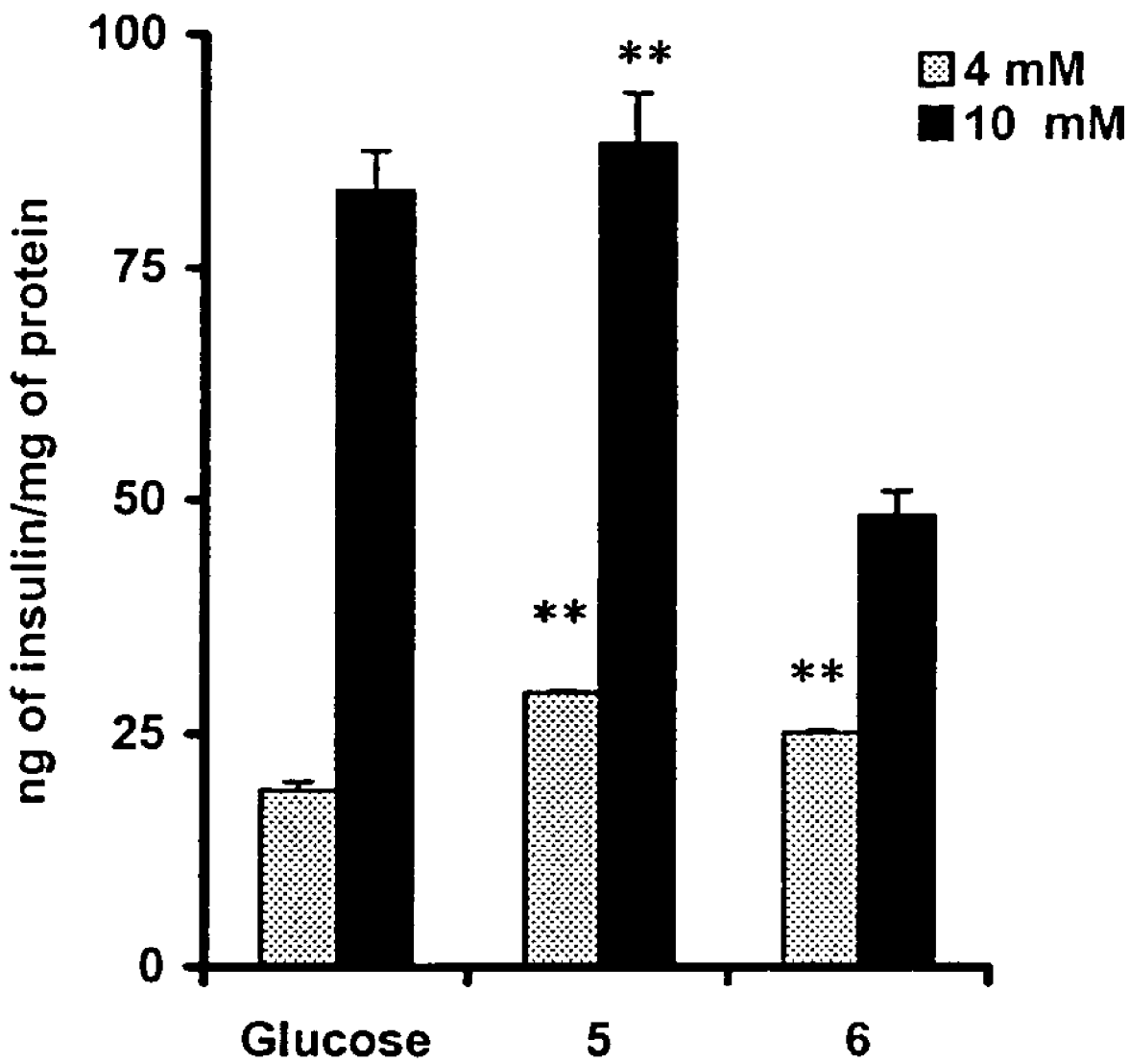

The anthocyanidins were assayed at 50 µg/mL concentration. The aglycone of cyanidin-3-glucoside, cyanidin (5), enhanced insulin secretion by 1.5 fold (29 ng/mg of protein) at 4 mM glucose whereas at 10 mM glucose it secreted 88 ng/mg of protein (FIG. 2B). The untreated cells at 4 and 10 mM glucose secreted 19 and 83 ng insulin/mg of protein, respectively, in this set of assay. The aglycone delphinidin (6) showed an increase in insulin secretion by 6 ng/mg of protein at 4 mM glucose concentration and was not significant. Delphinidin did not show glucose-induced insulin secretion at 10 mM glucose (FIG. 2B). Pelargonidin was the most active anthocyanidin and it secreted 49 (1.4 fold) and 91 (1.2 fold) ng of insulin/mg of protein at 4 and 10 mM glucose, respectively (FIG. 3). The aglycone petunidin (9) increased insulin secretion by 4 ng of insulin/mg protein at 4 mM glucose concentration. However, malvidin (8) did not show an increase in insulin secretion with respect to the untreated cells.

Reports indicate that consumption of fruits and vegetables, especially rich in polyphenols, decreased the incidence of type-2 diabetes (Anderson, R. A., et al., *J. Agric. Food Chem.* 50 7182-7186 (2002); Anderson, R. A., et al., *J. Agric. Food Chem.* 52 65-70 (2004); and Landrault, N., et al., *J. Agric. Food Chem.* 51 311-3188 (2003)). Also, it is known that dietary antioxidants protect pancreatic β-cells from glucose-induced oxidative stress. Anthocyanins are abundant in fruits, vegetables and processed food products such as wine, cider and tea; however, little is known of its ability to reduce or prevent diabetes. Our results suggested that both anthocyanins and anthocyanidins are insulin secretagogues. The most potent among them was delphinidin-3-glucoside and it significantly induced the insulin secretion at 4 and 10 mM glucose concentrations compared to the untreated cells. Although cyanidin-3-glucoside was less active than delphinidin-3-glucoside at lower glucose concentration, it was more active at higher glucose concentration. Among the galactosides, pelargonidin-3-galactoside did not induce insulin secretion at 4 and 10 mM glucose concentrations studied where as cyanidin-3-galactoside showed significant increase in insulin secretion. The ability of anthocyanins studied to secrete insulin was in the increasing order of delphinidin-3-glucoside>cyanidin-3-glucoside>pelargonidin-3-galactoside. This indicated that the number of hydroxyl groups in ring-B of anthocyanins played an important role in their ability to secrete insulin. Among the anthocyanidins tested, pelargonidin was the most active at 4 mM glucose. Other aglycones did not potentiate significant insulin secretion at 4 or 10 mM glucose concentrations studied.

This is the first report of insulin secretion by anthocyanins and anthocyanidins when exposed to pancreatic beta cells. Our results suggest that *Cornus* fruits, cherries and berries containing these anthocyanins are useful for the prevention of type-2 diabetes. Also, isolated and purified anthocyanins and anthocyanidins from fruits and vegetables may be useful to treat type-2 diabetes.

LITERATURE CITED (1) Ross, S. A.; Gulve, E. A.; Wang, M. Chemistry and Biochemistry of diabetes. Chem. Rev. 2004, 104, 1255-1282.
(2) Jovanovic, L.; Gondos, B. Type-2 diabetes: The epidemic of new millennium. Ann. Clin. Lab. Sci. 1999, 29, 33-42.
(3) Henquin, J. C. Triggering and amplifying pathways of regulation of insulin secretion by glucose. Diabetes 2000, 49, 1751-1760.
(4) Pfeiffer, A. F. H. Oral hypoglycemic agents: Sulfonylureas and meglitinides. In B. J. Goldstein, D. Müller-Wieland (Eds.), Text book of Type-2 Diabetes. Martin Dunitz Ltd., London, 2003, pp. 77-85.
(5) Blakely, S.; Herbert, A.; Collins, M.; Jenkins, M.; Mitchell, G.; Grundel, E.; O'Neill, K. R.; Khachik, F. Lutein interacts with ascorbic acid more frequently than with $\alpha$-tocopherol to alter biomarkers of oxidative stress in female Zucker obese rats. J. Nutr. 2003, 133, 2838-2844.
(6) Jayaprakasam, B.; Strasburg, G. A.; Nair, M. G. Potent lipid peroxidation inhibitors from Withania somnifera. Tetrahedron 2004, 60, 3109-3121.
(7) Duthie, G. G.; Duthie, S. J.; Kyle, J. A. M. Plant polyphenols in cancer and heart disease: implications as nutritional antioxidants. Nutr. Res. Rev. 2000, 13, 79-106.
(8) Kang, S. Y.; Seeram, N. P.; Nair, M. G.; Bourquin, L. D. Tart cherry anthocyanins inhibit tumor development in ApcMin mice and reduce proliferation of human colon cancer cells. Canc. Lett. 2003, 194, 13-19.
(9) Van Velden, D. P.; Mansvelt, E. P. G.; Fourie, E.; Rossouw, M.; Marais, A. D. The cardioprotective effect of wine on human blood chemistry. Ann. New York Acad. Sci. 2002, 957, 337-340.
(10) Wang, H.; Nair, M. G.; Strasburg, G. M.; Chang, Y. C.; Booren, A. M.; Gray, I. J.; DeWitt, D. L. Antioxidant and antiinflammatory activities of anthocyanins and their aglycone, cyanidin, from tart cherries. J. Nat. Prod. 1999, 62, 294-296.
(11) Tsuda, T.; Horio, F.; Uchida, K.; Aoki, H.; Osawa, T. Dietary cyanidin 3-O-β-D-glucoside-rich purple corn color prevents obesity and ameliorates hyperglycemia in mice. J. Nut. 2003, 133, 2125-2130.
(12) Espin, J. C.; Soler-Rivas, C.; Wichers, H. J.; Garcia-Viguera, C. Anthocyanin-based natural colorants. A new source of antiradical activity for foodstuff. J. Agri. Food Chem. 2000, 48, 1588-1592.
(13) Millspaugh, C. F. In American Medicinal Plants; Dover Publications: New York, 1974; p 282.
(14) Kim, D. K.; Kwak, J. H. A Furan derivative from Cornus officinalis. Arch. Pharm. Res. 1998, 21, 787-789.
(15) Yamahara, J.; Mibu, H.; Sawada, T.; Fujimura, H.; Takino, S.; Yoshikawa, M.; Kitagawa, I. Biologically active principles of crude drugs. Antidiabetic principles of corni fructus in experimental diabetes induced by streptozotocin. Yakugaku Zasshi 1981, 101, 86-90.
(16) Seeram, N. P.; Schutzki, R.; Chandra, A.; Nair, M. G. Characterization, Quantification, and Bioactivities of Anthocyanins in Cornus Species. J. Agri. Food Chem. 2002, 50, 2519-2523.
(17) Beckwith, A. G.; Zhang, Y.; Seeram, N. P.; Cameron, A. C.; Nair, M. G. Relationship of Light Quantity and Anthocyanin Production in Pennisetum setaceum Cvs. Rubrum and Red Riding Hood. J. Agric. Food Chem. 2004, 52, 456-461.
(18) Hohmeier, H. E.; Mulder, H.; Chen, G.; Henkel-Rieger, R.; Prentki, M.; Newgard, C. B. Isolation of INS-1-derived cell lines with robust ATP-sensitive K+ channel-dependent and -independent glucose-stimulated insulin secretion. Diabetes 2000, 49, 424-430.
(19) Francis, J. A.; Jayaprakasam, B.; Olson, L. K.; Nair, M. G. Insulin secretagogues from Moringa oleifera with cyclooxygenase enzyme and lipid peroxidation inhibitory activities. Helv. Chim. Acta 2004, 87, 317-326.
(20) Christison, G. B.; MacKenzie, H. A. Laser photoacoustic determination of physiological glucose concentrations in human whole blood. Med. Boil. Eng. Comp. 1993, 31, 284-90.
(21) Anderson, R. A.; Polansky, M. M. Tea Enhances Insulin Activity. J. Agric. Food Chem. 2002, 50, 7182-7186.
(22) Anderson, R. A.; Broadhurst, C. L.; Polansky, M. M.; Schmidt, W. F.; Khan, A.; Flanagan, V. P.; Schoene, N. W.; Graves, D. J. Isolation and Characterization of Polyphenol Type-A Polymers from Cinnamon with Insulin-like Biological Activity. J. Agric. Food Chem. 2004, 52, 65-70.
(23) Landrault, N.; Poucheret, P.; Azay, J.; Krosniak, M.; Gasc, F.; lenin, C.; Cros, G.; Teissedre, P. Effect of a Polyphenols-Enriched Chardonnay White Wine in Diabetic Rats. J. Agric. Food Chem. 2003, 51, 311-318.

The methods for the separation of and production of the anthocyanins and anthocyanidins are described in U.S. Pat. Nos. 6,194,469; 6,423,365; 6,623,743; 6,676,978 and 6,656,914; and U.S. patent application Ser. No. 10/084,575, filed Feb. 27, 2002 which are incorporated by reference herein in their entireties.

It is intended that the foregoing description be only illustrative of the present invention and that the present invention be limited only by the hereinafter appended claims.

We claim:

1. A method for increasing insulin concentration secreted by pancreatic beta cells comprising:
    providing to the pancreatic cells in the presence of glucose at a glucose concentration between a normal human glucose level and an elevated human glucose level of 2.5 times the normal human glucose level a composition of a purified mixture consisting of at least two molecules having structures where R is H, glucosyl or galactosyl; R' is H, OH or OCH$_3$; and R" is H, OH or OCH$_3$ with the proviso that when R is H, then R' is not OCH$_3$ or R" is not OCH$_3$ or both R' and R" are not OCH$_3$ wherein one of the at least two molecules has R is galactosyl, R' is OH, and R" is H and is cyanidin-3-galactoside or one of the at least two molecules has R is galactosyl, R' is H, and R" is H and is pelargonidin-3-galactoside; and
    allowing the composition to increase the insulin concentration secreted by the pancreatic cells.

2. The method of claim 1 wherein the pancreatic cells an in vivo.

3. The method of claim 1 wherein one of the at least two molecutes has R is glucosyl, R' is OH, and R" is OH and is delphinidin-3-glucoside.

4. The method of claim 1 further comprising isolating the at least two molecutes from *Cornus mas L.*

5. The method of claim 1 wherein one of the at least two molecules has R is glucosyl, R' is OH, and R" is H and is cyanidin-3-glucoside.

6. The method of claim 1 wherein one of the at least two molecules has R is H, R' is OH, and R" is OH and is delpihnidin.

7. The method of claim 1 wherein the composition increases the insulin concentration by a factor of between 1.2 and 1.8.

8. The method of claim 1 wherein one of the at least two molecules has R is H, R' is H, and R" is H and is pelargonidin.

9. The method of claim 1 wherein one of the at least two molecules has R is H, R' is OH, and R" is H and is cyanidin.

10. The method of claim 1 wherein one of the at least two molecules has R is galactosyl, R' is OH, and R" is H and is cyanidin-3-galactoside and a second of the at least two molecules has R is glucosyl, R' is OH, and R" is OH and is delphinidin-3-glucoside.

11. The method of claim 10 wherein a third of the at least two molecules has R is galactosyl, R' is H, and R" is H and is pelardonidin-3-galactoside.

12. The method of claim 1 further comprising isolating the at least two molecules from fruits.

13. The method of claim 1 further comprising isolating the at least two molecules from vegetables.

* * * * *